United States Patent
Ohtsuka

(10) Patent No.: US 10,184,788 B2
(45) Date of Patent: Jan. 22, 2019

(54) OPTICAL FIBER SENSOR SYSTEM HAVING A POLARIZATION SEPARATOR

(71) Applicant: Sumitomo Electric Industries, Ltd., Osaka-shi (JP)

(72) Inventor: Takafumi Ohtsuka, Yokohama-shi (JP)

(73) Assignee: Sumitomo Electric Industries, Ltd., Osaka-shi (JP)

( * ) Notice: Subject to any disclaimer, the term of this patent is extended or adjusted under 35 U.S.C. 154(b) by 216 days.

(21) Appl. No.: 15/046,837

(22) Filed: Feb. 18, 2016

(65) Prior Publication Data

US 2016/0238376 A1    Aug. 18, 2016

(30) Foreign Application Priority Data

Feb. 18, 2015  (JP) ................................. 2015-029612

(51) Int. Cl.
| | |
|---|---|
| *G01B 11/16* | (2006.01) |
| *G02F 1/01* | (2006.01) |
| *G01N 29/14* | (2006.01) |
| *G02B 6/27* | (2006.01) |

(Continued)

(52) U.S. Cl.
CPC .......... *G01B 11/161* (2013.01); *G01B 11/168* (2013.01); *G01N 29/043* (2013.01); *G01N 29/14* (2013.01); *G01N 29/2418* (2013.01); *G02B 6/2706* (2013.01); *G02B 6/2766* (2013.01); *G01N 2291/023* (2013.01); *G01N 2291/0289* (2013.01)

(58) Field of Classification Search
CPC .. G01B 11/161; G01B 11/168; G01N 29/043; G01N 29/14; G01N 29/2418; G01N 2291/023; G01N 2291/0289; G02B 6/2706; G02B 6/2766
USPC ............................................................ 73/587
See application file for complete search history.

(56) References Cited

U.S. PATENT DOCUMENTS

| | | | | |
|---|---|---|---|---|
| 4,735,506 A | * | 4/1988 | Pavlath ................ | G01C 19/726 356/464 |
| 5,717,489 A | * | 2/1998 | Ozeki ..................... | G01J 3/447 250/225 |

(Continued)

FOREIGN PATENT DOCUMENTS

JP    2008-309776 A    12/2008

*Primary Examiner* — Natalie Huls
*Assistant Examiner* — Monica S Young
(74) *Attorney, Agent, or Firm* — Venable LLP; Michael A. Sartori; Laura G. Remus

(57) ABSTRACT

The optical fiber sensor system includes a light source unit including a light source and a polarization controller, a modulation unit having an optical path and a coil and configured to modulate light passing though the optical path according to stress applied to the coil, an optical coupler configured to branch the measured light into clockwise light and counterclockwise light, and output interference light, a polarization separator configured to separate the interference light into a first component and a second component having polarization states orthogonal to each other, and a detection unit having a first light detector and configured to detect stress by converting the first component into a first electrical signal. The polarization controller controls a polarization state of light output from the light source so that the first electrical signal is proportional to the stress.

5 Claims, 4 Drawing Sheets

(51) Int. Cl.
  *G01N 29/04* (2006.01)
  *G01N 29/24* (2006.01)

(56) References Cited

U.S. PATENT DOCUMENTS

| | | | | |
|---|---|---|---|---|
| 2003/0038946 | A1* | 2/2003 | Takashima | G01H 9/004 356/483 |
| 2004/0141420 | A1* | 7/2004 | Hardage | E21B 47/00 367/149 |
| 2005/0225746 | A1* | 10/2005 | Nishikawa | G01M 11/333 356/73.1 |
| 2010/0281985 | A1* | 11/2010 | Kumagai | G01H 9/004 73/655 |
| 2013/0033709 | A1* | 2/2013 | Potin | G01B 11/26 356/492 |
| 2014/0025319 | A1* | 1/2014 | Farhadiroushan | G01S 5/186 702/56 |

\* cited by examiner

OPTICAL FIBER SENSOR SYSTEM HAVING A POLARIZATION SEPARATOR

BACKGROUND OF THE INVENTION

The present invention relates to an optical fiber sensor system.

Japanese Unexamined Patent Publication No. 2008-309776 discloses an optical fiber vibration sensor including a light source, a light receiver, an optical branching and coupling unit having a polarizer, and a fiber loop unit. The light source and the polarizer are optically coupled each other and light controlled so that a polarization state is uniform through the polarizer is output to the fiber loop unit via a coupler. Clockwise light and counterclockwise light propagate into the fiber loop unit. The clockwise light and the counterclockwise light are re-coupled and interfere with each other in the coupler and interference light is obtained. The interference light is received by the light receiver and converted into an electrical signal. When an acoustic signal is applied to the fiber loop, phase differences different from each other are applied to the clockwise light and the counterclockwise light, and the interference state of the interference light changes. The light receiver receives the interference light in which the interference state changes, and therefore stress applied to the fiber loop is detected.

SUMMARY OF THE INVENTION

An optical fiber sensor system according to an aspect of the present invention is an optical fiber sensor system including a light source unit including a light source and a polarization controller and configured to output measured light; a modulation unit having a loop-shaped optical path and a coil around which the optical path is wound and configured to modulate light passing through the optical path according to stress applied to the coil; an optical coupler optically coupled to the light source unit and both ends of the optical path and configured to input the measured light, branch the measured light into first light and second light having polarization states different from a polarization state of the measured light, output the first light from one end of the optical path to the other end, output the second light from the other end of the optical path to the one end, and couple the first light input to the other end and the second light input to the one end to output interference light; a polarization separator optically coupled to the optical coupler and configured to input the interference light output from the optical coupler and separate the interference light into a first component and a second component having polarization states orthogonal to each other to output the first and second components; and a detection unit optically coupled to the polarization separator, having a first light detector to which the first component output from the polarization separator is input, and configured to detect stress by converting the first component input to the first light detector into a first electrical signal, wherein the polarization controller controls the polarization state of light output from the light source so that the first electrical signal is proportional to the stress.

DESCRIPTION OF EMBODIMENTS

Figure 1:
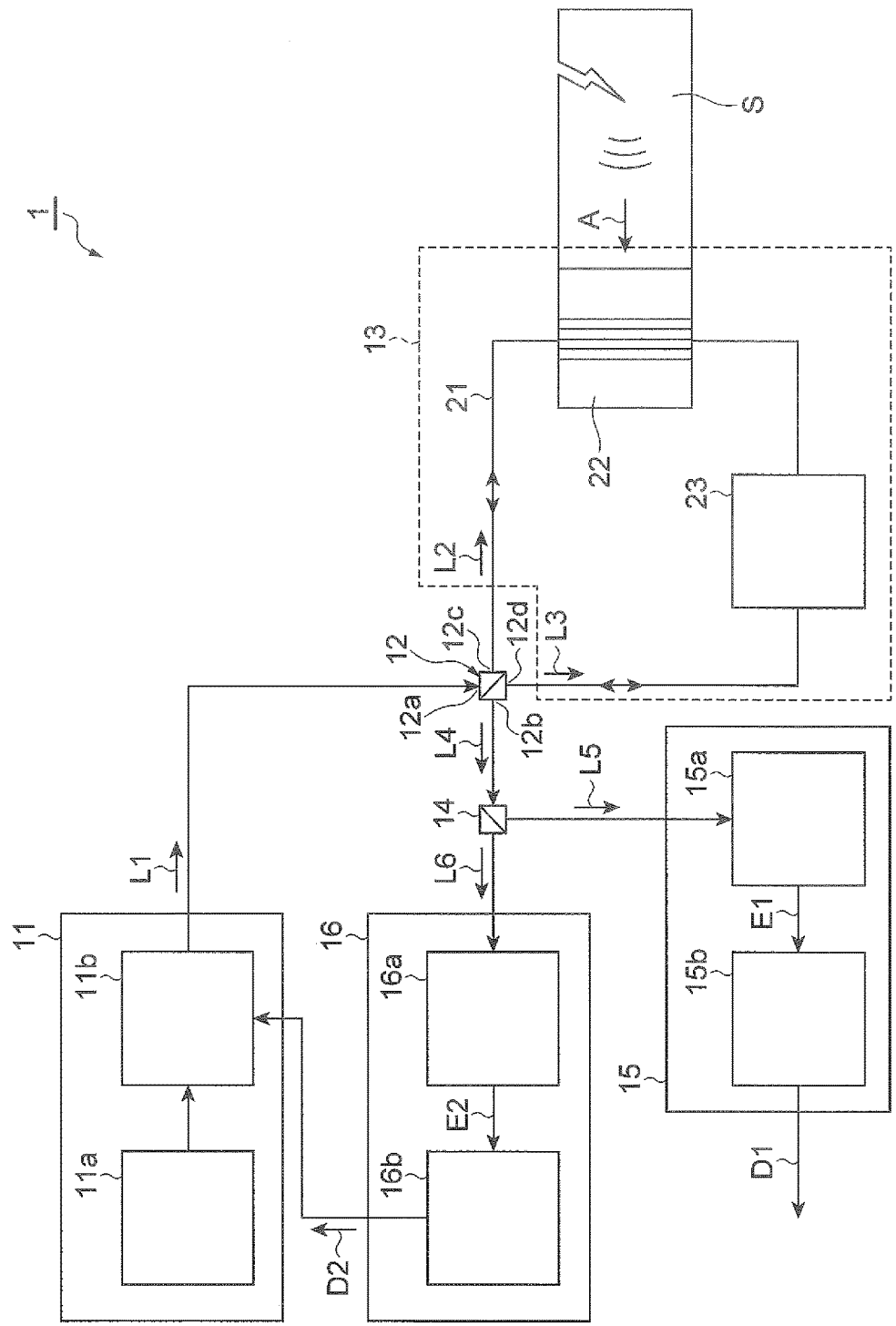
FIG. 1 is a diagram illustrating an optical fiber sensor system according to an embodiment.

Description of Embodiments of the Present Invention

First, content of the embodiments of the present invention will be listed and described. (1) An optical fiber sensor system according to an aspect of the present invention is an optical fiber sensor system including a light source unit including a light source and a polarization controller and configured to output measured light; a modulation unit having a loop-shaped optical path and a coil around which the optical path is wound and configured to modulate light passing through the optical path according to stress applied to the coil; an optical coupler optically coupled to the light source unit and both ends of the optical path and configured to input the measured light, branch the measured light into first light and second light having polarization states different from a polarization state of the measured light, output the first light from one end of the optical path to the other end, output the second light from the other end of the optical path to the one end, and couple the first light input to the other end and the second light input to the one end to output interference light; a polarization separator optically coupled to the optical coupler and configured to input the interference light output from the optical coupler and separate the interference light into a first component and a second component having polarization states orthogonal to each other to output the first and second components; and a detection unit optically coupled to the polarization separator, having a first light detector to which the first component output from the polarization separator is input, and configured to detect stress by converting the first component input to the first light detector into a first electrical signal, wherein the polarization controller controls the polarization state of light output from the light source so that the first electrical signal is proportional to the stress.

In this optical fiber sensor system, the polarization controller outputs the measured light by controlling a polarization state of light output from the light source so that the first electrical signal includes a component which is proportional to a stress by an acoustic signal. Accordingly, it is possible to detect a weak acoustic signal with high sensitivity.

(2) Also, the optical fiber sensor system may include a control unit optically coupled to the polarization separator and configured to input the second component output from the polarization separator to convert the second component into a second electrical signal and output a control signal for controlling the polarization controller on the basis of the second electrical signal. Thereby, it is possible to control the polarization state of the measured light on the basis of the second component. Also, a light intensity of the first component can be controlled by controlling a light intensity of the second component. Thereby, it is possible to detect the acoustic signal with high sensitivity.

(3) Also, the control unit may include a second light detector to which the second component is input and control the polarization controller so that the light intensity of the second component input to the second light detector is minimized. Thereby, the polarization controller is controlled so that the light intensity of the first component is maximized. Accordingly, it is possible to detect the acoustic signal with high sensitivity.

(4) Also, the control unit may include a second processing unit configured to generate the control signal by suppressing a high-frequency component included in the second electrical signal relative to a low-frequency component. Thereby, a control signal obtained by removing the high-frequency component corresponding to the applied acoustic signal is input to the polarization controller. Accordingly, it is possible to improve the quality of the control signal input to the polarization controller.

(5) Also, the detection unit may include a first processing unit configured to suppress a low-frequency component included in the first electrical signal relative to a high-frequency component, and the first processing unit may output a detection signal for detecting the stress. Thereby, the low-frequency component serving as noise is removed from the first electrical signal. Also, it is possible to amplify the high-frequency component serving as a detection signal of the acoustic signal. Accordingly, it is possible to improve an SN ratio of the detection signal of the acoustic signal.

(6) Also, the optical coupler may have two inputs and two outputs. Thereby, it is possible to allocate ports of the optical coupler to an input of the measured light, an output of the interference light, and one end and the other end of the optical path, and suppress the occurrence of optical loss.

(7) Also, the measured light output from the light source unit may be linearly polarized light, the optical coupler may branch the measured light into first light and second light which are circularly polarized light, the modulation unit may have an optical rotation property and convert the first light and the second light into elliptically polarized light, and the optical coupler may couple the first light and the second light which are the elliptically polarized light to output the interference light which is elliptically polarized light different from the first light and the second light. Thereby, it is possible to efficiently generate the first component including a component which is proportional to a stress by the acoustic signal.

Description of Embodiments of the Present Invention

Specific examples of the optical fiber sensor system according to the embodiments of the present invention will be described with reference to the drawings. Also, the present invention is not limited to the examples, but is intended to include all changes and modifications within the scope of claims and the equivalent scope. In the following description, the same elements are assigned the same reference signs in the description of the drawings and redundant description thereof will be omitted.

FIG. 1 illustrates a configuration of an optical fiber sensor system 1 according to the embodiment. The optical fiber sensor system 1 is, for example, an optical fiber acoustic sensor to be used for soundness diagnosis of a structure and detects an acoustic emission (AE) generated when the structure cracks. The optical fiber sensor system 1 includes a light source unit 11, an optical coupler 12, a modulation unit 13, a polarization separator 14, a detection unit 15, and a control unit 16.

The light source unit 11 includes a light source 11a and a polarization controller 11b. The light source unit 11 is optically coupled to the optical coupler 12. In this embodiment, a broadband light source in which a coherent length is short can be used as the light source 11a because an optical path length difference of an interference system is removed in principle as will be described below. When the broadband light source is used as the light source 11a, it is possible to improve resistance to reflected light noise, etc.

The polarization controller 11b inputs light output by the light source 11a. The polarization controller 11b outputs measured light L1 by controlling a polarization state of the light input from the light source 11a. Control of the polarization state in the polarization controller 11b will be described below.

The optical coupler 12 is an optical coupler of two inputs and two outputs having four ports 12a, 12b, 12c, and 12d. The port 12a and the light source unit 11 are optically coupled, and the measured light L1 output from the light source unit 11 is input to the port 12a. The optical coupler 12 branches the measured light L1 into clockwise light (first light) L2 and counterclockwise light (second light) L3. The measured light L1, the clockwise light L2, and the counterclockwise light L3 have different polarization states.

The modulation unit 13 includes a loop-shaped optical path 21 for coupling the port 12c and the port 12d, a coil 22 around which the optical path 21 is wound, and a delay path 23 provided at a point along the optical path 21. One end of the optical path 21 is connected to the port 12c, and the other end of the optical path 21 is connected to the port 12d. The clockwise light L2 is output from the port 12c and input to the port 12d through the delay path 23 after passing through the coil 22. The counterclockwise light L3 is output from the port 12d and input to the port 12c through the coil 22 after passing through the delay path 23.

The optical coupler 12 combines the clockwise light L2 input to the port 12d and the counterclockwise light L3 input to the port 12c and outputs interference light L4 from the port 12b. The optical path 21 includes an optical fiber and is configured to have an optical rotation property. Accordingly, the clockwise light L2 and the counterclockwise light L3 output from the ports 12c and 12d and the interference light L4 output from the port 12b have different polarization states. Also, because the clockwise light L2 and the counterclockwise light L3 propagate through the same optical path 21, optical path lengths of the clockwise light L2 and the counterclockwise light L3 are the same. Thus, the optical coupler 12 and the modulation unit 13 of this embodiment constitute a Sagnac interferometer.

Figure 2:
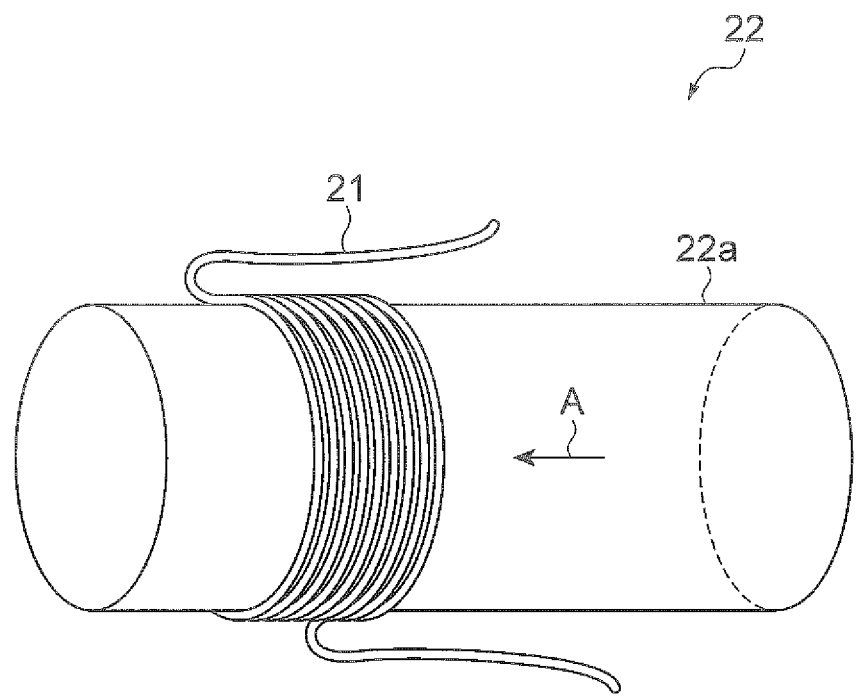
FIG. 2 is a diagram illustrating a coil which functions as a sensor head.

As illustrated in FIG. 2, the coil 22 has a core 22a around which the optical path 21 is spirally wound. The coil 22 is attached to a structure S serving as a measurement target and functions as a sensor head of the optical fiber sensor system 1. The structure S emits an acoustic signal by a mechanical fracture, etc. and expands and contracts the optical path 21 via the coil 22. At this time, a refractive index of the optical fiber constituting the optical path 21 slightly changes according to stress applied to the coil 22, and optical path lengths of the clockwise light L2 and the counterclockwise light L3 change. As a result, phase modulation occurs in the clockwise light L2 and the counterclockwise light L3.

FIG. 1 will be referred to again. The delay path 23 delays the clockwise light L2 and the counterclockwise light L3. The delayed clockwise light L2 is directly output to the optical coupler 12. On the other hand, the delayed counterclockwise light L3 is output to the optical coupler 12 through the coil 22. Accordingly, the timing of modulation applied to the clockwise light L2 according to the stress and the timing of modulation applied to the counterclockwise light L3 according to the stress are different from each other. In this embodiment, the delay path 23 is arranged along a forward path of the counterclockwise light L3. Consequently, an acoustic signal propagates in the counterclockwise light L3 at a time t later than the clockwise light L2.

The polarization separator 14 is optically coupled to the port 12b of the optical coupler 12. The interference light L4 output from the port 12b is input to the polarization separator 14. The clockwise light L2, the counterclockwise light L3, and the interference light L4 have mutually different polarization states. The polarization separator 14 separates the input interference light L4 into a first component L5 and a second component L6 having polarization states orthogonal to each other, and outputs the first component L5 and the second component L6.

The detection unit 15 is optically coupled to the polarization separator 14. The first component L5 output from the polarization separator 14 is input to the detection unit 15 and a detection signal D1 for detecting the acoustic signal is generated. The detection unit 15 includes a first light detector 15a and a first processing unit 15b. The first light detector 15a converts a light intensity of the input first component L5 into a voltage value, and outputs a first electrical signal E1. The first processing unit 15b generates the detection signal D1 by suppressing an intensity or amplitude of a low-frequency component (for example, a frequency component less than $1/10^{th}$ of the frequency of the acoustic signal to be measured) included in the first electrical signal E1 relative to a high-frequency component (for example, a frequency component greater than $1/10^{th}$ of the frequency of the acoustic signal to be measured). The first processing unit is, for example, a high-frequency amplifier configured to amplify a high-frequency component of the first electrical signal E1.

The control unit 16 is optically coupled to the polarization separator 14. The second component L6 output from the polarization separator 14 is input to the control unit 16 and a control signal D2 for controlling the polarization controller 11b is generated and input to the polarization controller 11b. The control unit 16 includes a second light detector 16a and a second processing unit 16b. The second light detector 16a converts an intensity of the input second component L6 into a voltage value, and outputs a second electrical signal E2. The second processing unit 16b is, for example, a low-frequency amplifier configured to generate the control signal D2 by removing the high-frequency component (for example, the high-frequency component greater than $1/10^{th}$ of the frequency of the acoustic signal to be measured) from the second electrical signal E2.

Figure 3A:
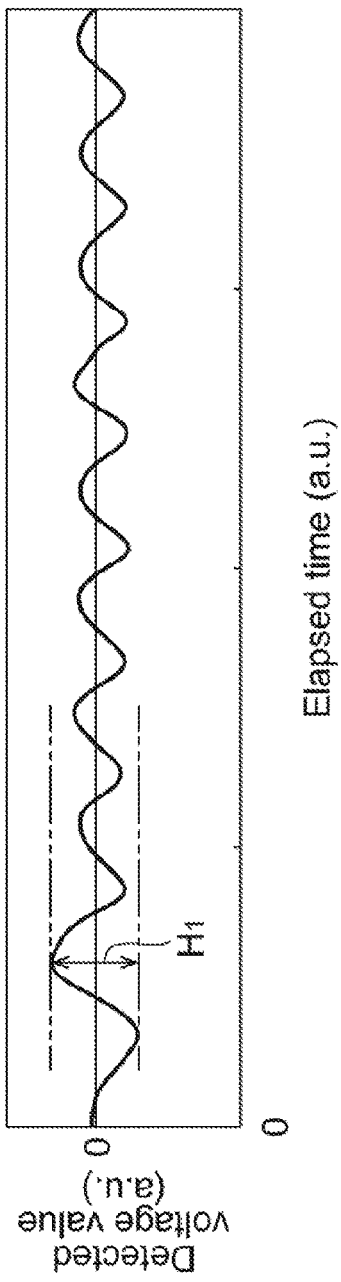
FIG. 3A is a graph illustrating time-series data of a voltage value detected by a first light detector.
Figure 3B:
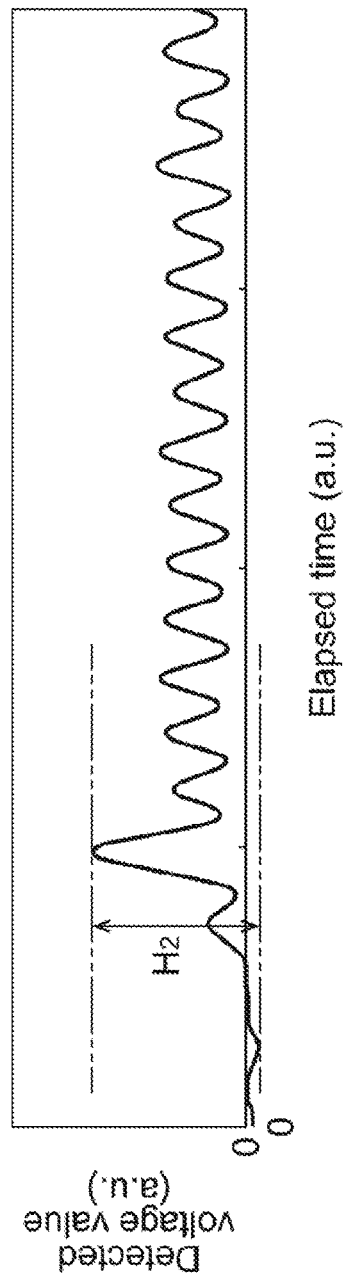
FIG. 3B is a graph illustrating time-series data of a voltage value detected by a second light detector.

FIGS. 3A and 3B illustrates time-series data of a detected voltage value when a predetermined acoustic signal is applied to the coil 22. FIG. 3A illustrates the first electrical signal E1 and FIG. 3B illustrates the second electrical signal E2. In FIGS. 3A and 3B, the detected voltage value is an averaged value for each fixed time (for example, 10 μs) and a difference between a maximum value and a minimum value of the detected voltage value within a predetermined time is defined as wave height values $H_1$ and $H_2$. The relationships between the wave height values $H_1$ and $H_2$ and the stress applied to the coil 22 are illustrated in FIGS. 4A and 4B.

In the second electrical signal E2 illustrated in FIG. 3B, a change cycle of the detected voltage value is double the voltage value of the first electrical signal E1 illustrated in FIG. 3A, and a value less than or equal to zero is removed. That is, the detected voltage value of the second electrical signal E2 is proportional to the square of the sine of an amount of phase modulation based on stress. On the other hand, the detected voltage value of the first electrical signal E1 is proportional to the sine of the amount of phase modulation.

Figure 4A:
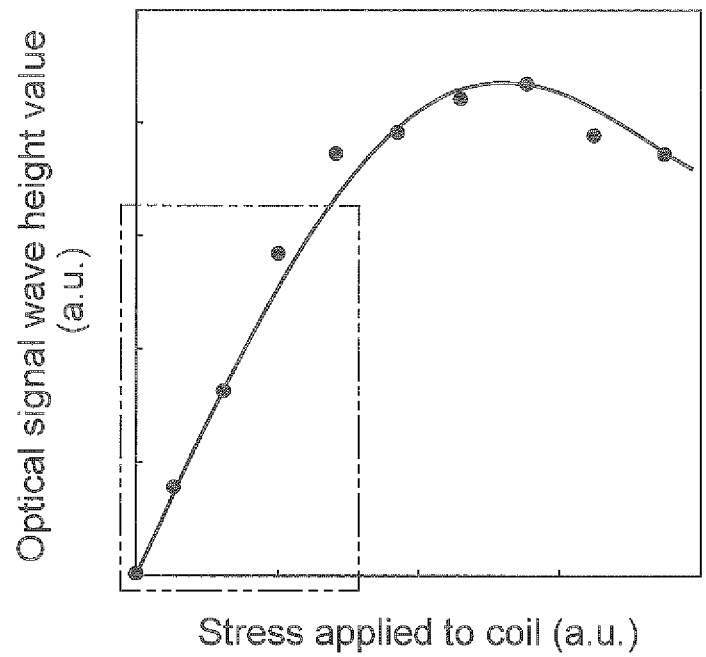
FIG. 4A is a graph illustrating a relationship between applied stress and a wave height value of an electrical signal by the first light detector.
Figure 4B:
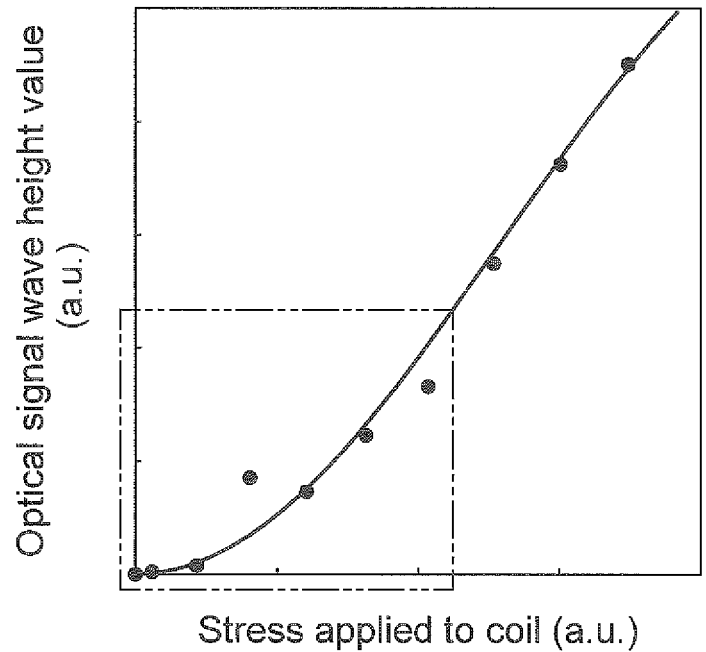
FIG. 4B is a graph illustrating a relationship between applied stress and a wave height value of an electrical signal by the second light detector.

FIG. 4A illustrates the relationship between the wave height value $H_1$ of the first electrical signal E1 and the stress by the acoustic signal applied to the coil 22. FIG. 4B illustrates the relationship between the wave height value $H_2$ and the stress by the acoustic signal applied to the coil 22. In the second electrical signal E2, it can be seen that the wave height value $H_2$ is proportional to the square of the stress in a region in which the stress, which is indicated by a two-dot chain line, is relatively small. On the other hand, in the first electrical signal E1, it can be seen that the wave height value $H_1$ is proportional to the stress in a region in which the stress, which is indicated by the two-dot chain line, is relatively small.

According to a magnitude of stress applied by the acoustic signal, amounts of phase modulation applied to the clockwise light L2 and the counterclockwise light L3 also change. From FIGS. 3A, 3B, 4A and 4B, it can be seen that the optical fiber sensor system 1 is configured to receive light of the first component L5 including a component which is proportional to the stress in the first light detector 15a and receive light of the second component L6 including a component which is proportional to the square of the stress in the second light detector 16a.

As described above, the present inventor discovered that the response behavior of the detection signal D1 for an acoustic signal A (the stress applied to the coil 22) changes by inputting the clockwise light L2 and the counterclockwise light L3 having different polarization states from the measured light L1 to the modulation unit 13 which is a Sagnac interferometer and separating and detecting a predetermined polarization component. Hereinafter, the actions and effects obtained from the optical fiber sensor system 1 having the above-described configuration will be described.

In the optical fiber sensor system 1, the measured light L1, in which the polarization state is controlled, is output from the light source unit 11 so that the interference light L4 including a component which is proportional to the stress is output by the acoustic signal. The polarization separator 14 branches the first component L5 including a component which is proportional to the stress for the acoustic signal, and inputs the branched first component L5 to the first light detector 15a. The polarization controller 11b controls the polarization state of light output from the light source so that the first electrical signal E1 including a component which is proportional to the stress. Accordingly, it is possible to detect a weak acoustic signal with high sensitivity.

The optical fiber sensor system 1 includes further the control unit 16 configured to input the second component L6 output from the polarization separator 14 to convert the second component L6 into the second electrical signal E2, and outputs the control signal D2 for controlling the polarization controller 11b on the basis of the second electrical signal E2. Thereby, it is possible to control the polarization state of the measured light L1 as described above on the basis of the second component L6. Also, it is also possible to control the intensity of the first component L5 which is input to the first light detector 15a by controlling the intensity of the second component L6. Thereby, it is possible to detect the acoustic signal with high sensitivity.

The control unit 16 includes the second light detector 16a to which the second component L6 is input, and controls the polarization controller 11b so that a light intensity of the second component L6 input to the second light detector 16a is minimized. Thereby, it is possible to maximize the optical intensity of the first component L5 input to the first light detector 15a. Accordingly, it is possible to detect the acoustic signal with high sensitivity.

The control unit 16 includes the second processing unit 16b configured to generate the control signal D2 by suppressing the high-frequency component included in the second electrical signal E2 relative to the low-frequency component. Thereby, the control signal D2 obtained by removing the high-frequency component corresponding to the acoustic signal is input to the polarization controller 11b. Accordingly, it is possible to improve quality of the control signal D2.

The detection unit 15 includes the first processing unit 15b configured to suppress the low-frequency component included in the first electrical signal E1 relative to the high-frequency component, and the first processing unit 15b outputs the detection signal D1 for detecting the stress by the acoustic signal. Thereby, it is possible to remove a low-frequency component serving as noise for the first electrical signal E1 or amplify a high-frequency component serving as the detection signal D1 of the acoustic signal. Accordingly, it is possible to improve an SN ratio of the detection signal D1.

The optical coupler 12 is an optical coupler of two inputs and two outputs. Thereby, it is possible to allocate the ports 12a to 12d of the optical coupler 12 to an input of the measured light L1, an output of the interference light L4, and one end and the other end of the optical path 21, and suppress the occurrence of optical loss.

As configuration of the optical fiber sensor system 1 for detecting an acoustic signal with highest sensitivity, the measured light L1 output from the light source unit 11 is linearly polarized light, and the optical coupler 12 branches the measured light L1 into the clockwise light L2 and the counterclockwise light L3 which are circularly polarized light, and outputs the clockwise light L2 and the counterclockwise light L3 to the coil 22. Further, the modulation unit 13 has an optical rotation property (for example, an optical rotation property of 45° or 45° multiplied by an odd number), and converts the clockwise light L2 and the counterclockwise light L3 which are circularly polarized light output from the optical coupler 12 into elliptically polarized light to output the elliptically polarized light to the optical coupler 12. The optical coupler 12 couples the clockwise light L2 and the counterclockwise light L3, which are the elliptically polarized light, and outputs the interference light L4 which is elliptically polarized light (for example, in which the polarization state is rotated by 90°) different from the clockwise light L2 and the counterclockwise light L3. After the optical coupler 12 and the modulation unit 13 are configured as described above, it is possible to efficiently generate a component having a polarization state being proportional to stress in the interference light L4 by controlling the polarization controller 11b so that the measured light L1 becomes circularly polarized light. Accordingly, it is possible to efficiently generate the first electrical signal E1 being proportional to the stress.

Although embodiments of the present invention have been described, the present invention is not limited to the above-described embodiments, but various modifications can be made without departing from the spirit and scope of the present invention. For example, in the above-described embodiment, the delay path 23 is arranged along the forward path of the counterclockwise light L3. However, an arrangement form of the delay path 23 is not limited to the above-described embodiment. For example, the delay path may be arranged along the forward path of the clockwise light L2.

What is claimed is:

1. An optical fiber sensor system comprising:
   a light source unit including a light source and a polarization controller, the light source unit being configured to output measured light;
   a modulation unit including a loop-shaped optical path and a coil around which the optical path is wound, the modulation unit being configured to modulate light passing through the optical path according to stress applied to the coil;
   an optical coupler optically coupled to the light source unit and both ends of the optical path and configured to input the measured light, branch the measured light into first light and second light having polarization states different from a polarization state of the measured light, output the first light from one end of the optical path to the other end, output the second light from the other end of the optical path to the one end, and couple the first light input to the other end and the second light input to the one end to output interference light;
   a polarization separator optically coupled to the optical coupler and configured to input the interference light output from the optical coupler and separate the interference light into a first component and a second component having polarization states orthogonal to each other to output the first and second components; and
   a detection unit optically coupled to the polarization separator, including a first light detector to which the first component output from the polarization separator is input, and configured to detect stress by converting the first component input to the first light detector into a first electrical signal,
   wherein the polarization controller controls the polarization state of light output from the light source so that the first electrical signal is proportional to the stress.

2. The optical fiber sensor system of claim 1, further comprising:
   a control unit optically coupled to the polarization separator, the control unit being configured to input the second component output from the polarization separator to convert the second component into a second electrical signal and output a control signal for controlling the polarization controller on the basis of the second electrical signal.

3. The optical fiber sensor system of claim 2,
   wherein the control unit includes a second light detector to which the second component is input and controls the polarization controller based on a light intensity of the second component input to the second light detector.

4. The optical fiber sensor system of claim 2,
   wherein the control unit includes a second light detector to which the second component is input and controls the polarization controller based on a light intensity of the second component input to the second light detector and not on a light intensity of the first component input to the first light detector.

5. The optical fiber sensor system of claim 1,
   wherein the measured light output from the light source unit is linearly polarized light,
   wherein the optical coupler branches the measured light into first light and second light which are circularly polarized light, wherein the modulation unit has an optical rotation property and converts the first light and the second light into elliptically polarized light, and wherein the optical coupler couples the first light and the second light which are the elliptically polarized light to output interference light which is elliptically polarized light different from the first light and the second light.

* * * * *